United States Patent [19]

Schoenwald et al.

[11] Patent Number: 4,866,083

[45] Date of Patent: * Sep. 12, 1989

[54] 2-T-BUTYL-3 ALKYL-5-(M-HYDROXYPHENYL)-1,3-OXAZOLIDINES HAVING MYDRIATIC EFFECT

[75] Inventors: Ronald D. Schoenwald, Iowa City, Iowa; Du-Shieng Chien, Costa Mesa, Calif.

[73] Assignee: University of Iowa Research Foundation, Iowa City, Iowa

[*] Notice: The portion of the term of this patent subsequent to Nov. 10, 2004 has been disclaimed.

[21] Appl. No.: 118,408

[22] Filed: Nov. 6, 1987

Related U.S. Application Data

[63] Continuation-in-part of Ser. No. 780,907, Sep. 27, 1985, Pat. No. 4,705,798.

[51] Int. Cl.$^4$ .................... A61K 31/42; C07D 498/10
[52] U.S. Cl. .................................... 514/374; 548/215
[58] Field of Search ......................... 548/215; 514/374

[56] References Cited

U.S. PATENT DOCUMENTS

| | | | |
|---|---|---|---|
| 2,243,295 | 5/1941 | Susie et al. | 548/215 |
| 4,028,368 | 6/1977 | Bodor et al. | 548/215 |
| 4,088,783 | 5/1978 | Bodor et al. | 548/215 |
| 4,158,005 | 6/1979 | Bodor et al. | 548/215 |
| 4,174,450 | 11/1979 | Bodor et al. | 548/215 |

Primary Examiner—Cecilia Shen
Attorney, Agent, or Firm—Zarley, McKee, Thomte, Voorhees & Sease

[57] ABSTRACT

An oxazolidine derivative of phenylephrine, and the non-toxic pharmaceutically acceptable salt forms thereof. The prodrug is much quicker absorbed across the cornea of the eye, does not induce the same unwanted side effects as phenylephrine, and can produce the same mydriatic effect as phenylephrine at dosage levels of approximately one-tenth the level of phenylephrine.

12 Claims, 1 Drawing Sheet

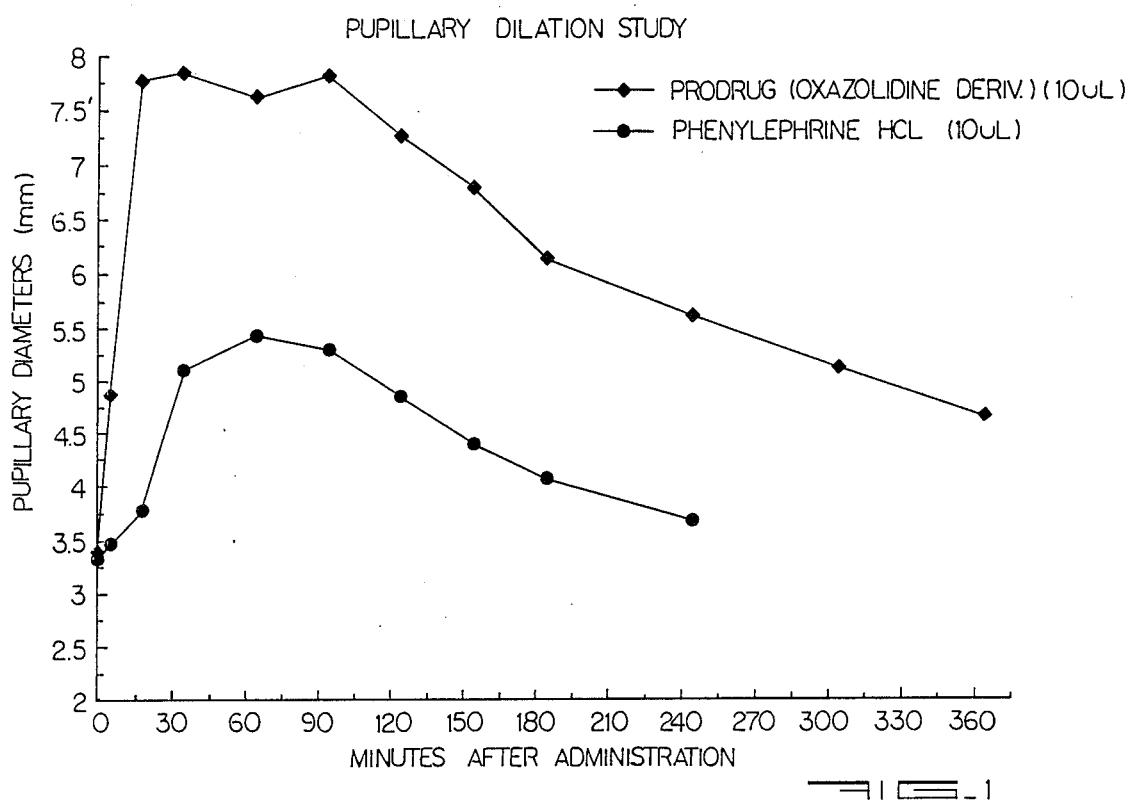
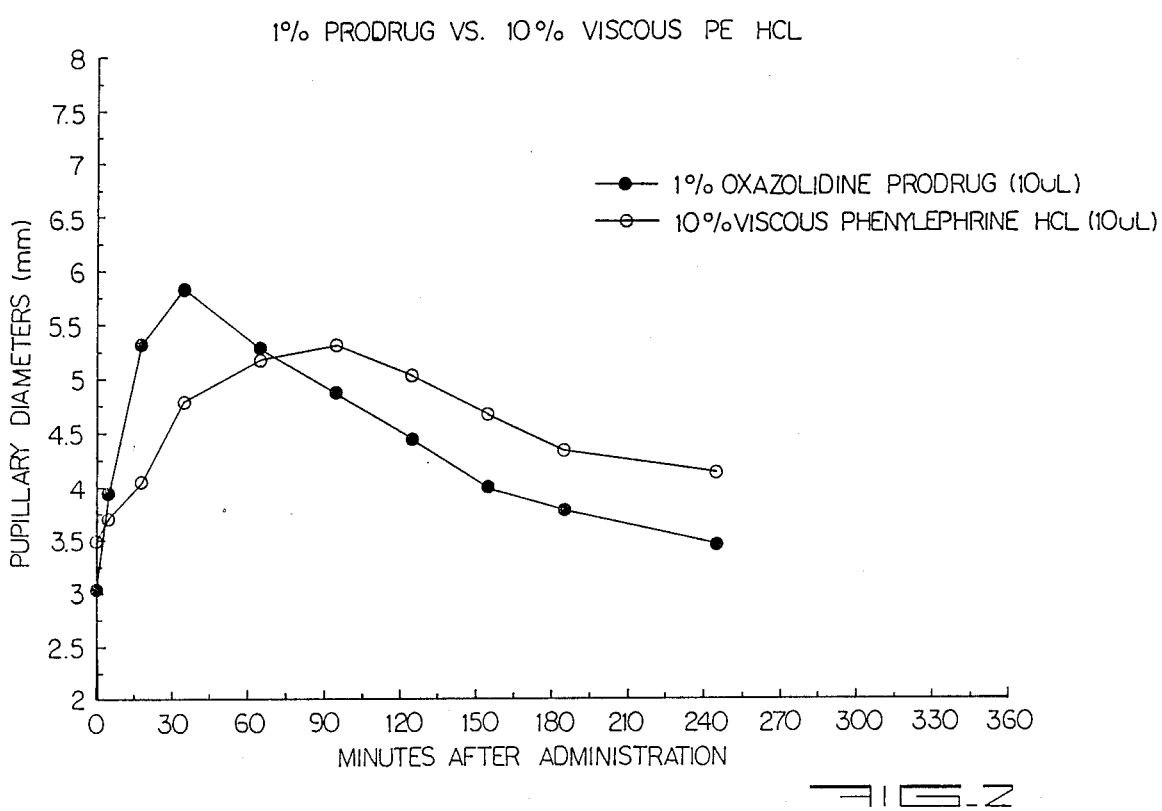

2-T-BUTYL-3 ALKYL-5-(M-HYDROXYPHENYL)-1,3-OXAZOLIDINES HAVING MYDRIATIC EFFECT

CROSS-REFERENCE TO A RELATED APPLICATION

This application is a continuation-in-part of our earlier filed co-pending application, Ser. No. 780,907, filed Sept. 27, 1985, now U.S. Letters Patent No. 4,705,798.

BACKGROUND OF THE INVENTION

The present invention relates to novel and therapeutic oxazolidine derivatives of 3-hydroxy-α-[(methylamino)methyl]-benzyl alcohol, commonly known as phenylephrine, and to pharmaceutical compositions containing the same.

Phenylephrine is a well-known pharmaceutically active amine whose principal use in the field of ophthalmology is as a mydriatic. There are, however, certain known disadvantages associated with the use of phenylephrine as a mydriatic agent. Those disadvantages have limited the use of this highly effective drug. Thus, in spite of the fact that it is one of the most effective mydriatics available, its use is significantly limited because of the significant side effects which may occur in some individuals treated with phenylephrine. Those unwanted significant side effects range from hypertension, syncope, and even in some cases to myocardial infarction, leading to death. Such side effects have been reported with doses of topical ocular phenylephrine.

One approach which has been used from time to time in the past is the effort to develop successful prodrugs of phenylephrine. As those skilled in the art know, the term prodrug refers to a therapeutic agent that requires enzymatic transformation to demonstrate therapeutic activity. In other words, the prodrug itself is not therapeutically active, but once subjected to enzymatic activity by the host organizism it is converted to an active drug. In the past there have been some attempts to make prodrugs of phenylephrine, with varying degrees of success. For example, Mindel et al, "Is Phenylephrine Pivalate a Prodrug?", *Arch. Ophthalmol.* 98, 2220 (1980) suggests the reaction product of phenylephrine and pivalic acid to provide a pivalic acid ester as a possible prodrug. However, as reported in that article, phenylephrine pivalate itself produces these side effects. And, it goes without saying that to have a successful prodrug, the prodrug itself must not produce the unwanted side effects, even though it may be effectively converted within the body to the active drug. Johansen et al, "Prodrugs as Drug Delivery Systems XXV: Hydrolysis of Oxazolidines—A Potential New Prodrug Type," *Journal Pharm. Sci.*, 72, 1294 (1983) discloses some prodrug possibilities of ephederine. However, ephederine is not commonly used ophthalmically and is biologically different in activity than phenylephrine, with ephederine being used orally for nacolepsy, bronchial asthma and nasal congestion. In contrast, the oxazolidine derivative of phenylephrine increases the bluk considerably on the amine function, the latter of which is responsible for phenylephrine's activity. With the addition of oxazolidine to the amine function, the prodrug would be expected to be devoid of alphaadrenergic activity (A. Burger, "Medicinal Chemistry, 3rd Ed., *Wiley-Interscience*, 1970, p. 1248).

Accordingly, there is a continuing and real need for safe and effective prodrugs of phenylephrine.

This invention has as its primary objective the development of novel and useful oxazolidine derivatives of phenylephrine, which when used at mydriatically effective levels does not produce side effects similar to phenylephrine, and at the same time is more quickly absorbed across the cornea than phenylephrine.

Another objective of the present invention is to provide a safe and pharmaceutically effective mydriatic which is a prodrug of phenylephrine, prepared from reacting phenylephrine with pivadehyde.

Yet another objective of the present invention is to prepare mydriatic compositions for topical occular treatment, useful in ophthalmic diagnosis and surgery.

Another objective of the present invention is to provide the compounds in a suitable non-aqueous vehicle that possesses increased stability and that can be administered in pharmaceutical formulations to produce a local or systemic physiological effect.

A further objective of the present invention is to provide a method of preparing a prodrug of phenylephrine which comprises reacting phenylephrine with pivaldehyde to produce a product which is stable in oil suspensions but which reverts to phenylephrine upon hydrolysis upon contact with tears.

The method and manner of accomplishing these and other objectives of the invention will become apparent from the detailed description which will follow hereinafter.

SUMMARY OF THE INVENTION

This invention relates to novel compounds which are prodrugs of phenylephrine useful as mydriatic agents. The prodrugs are oxazolidine derivatives of phenylephrine and in its preferred form constitutes 2-t-butyl-3-methyl-5-(m-hydroxyphenyl)-1,3-oxazolidine. The prodrugs are prepared by reacting phenylephrine with pivaldehyde. The reaction product is suspended in a non-toxic non-eye-irritating oil suspension in the preferred form, resulting in a mydriatic composition which does not have the typical side effects of phenylephrine, but at the same time is equally as effective at producing pupil dilation. It is more quickly absorbed across the cornea than phenylephrine and as a result can be used at dosages at levels down to one-tenth the amount of phenylephrine.

BRIEF DESCRIPTION OF THE DRAWINGS

FIG. 1 shows a pupillary dilation study for the prodrug of this invention in comparison with phenylephrine itself, with both at equal dose levels.

FIG. 2 shows a comparison of pupillary diameters for phenylephrine with the prodrug of this invention, with the prodrug at 1/10 the dose level of phenylephrine.

DETAILED DESCRIPTION OF THE INVENTION

One successfully obtains the objects of the present invention by employing as a mydriatic, a compound of the formula:

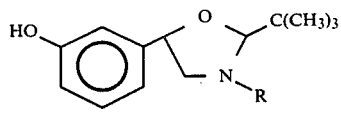

or the non-toxic pharmaceutically acceptable salt forms thereof. R is an alkyl group of $C_1$ to $C_5$.

This compound in its most preferred form (R=methyl) can also be conveniently named 2-t-butyl-3-methyl-5-(m-hydroxyphenyl)-1-,3-oxazolidine. Both the compound itself and its base form, or its pharmaceutically acceptable non-toxic acid salts thereof can be used. Such acid salt forms of biologically active compounds which are non-toxic are well-known and within the skill of the art. For example, such non-toxic salts include those derived from inorganic acids such as hydrochloric, hydrobromic, sulfuric, sulfamic, phosphoric, nitric, and the like; and the salts prepared from organic acids such acetic, propionic, succinic, glycollic, stearic, lactic, malic, tartaric, citric, ascorbic, pamoic, maleic, benzoic, glutamic and salicyclic.

Such pharmaceutically accepted salts of the base form of the compounds depicted in the previously presented formula can be synthesized by conventional, chemical methods. Generally, the salts are prepared by reacting the free base form with stoiciometric amounts or with an excess thereof of the desired salt forming inorganic or organic acid, in a suitable solvent, or various combinations of solvents. For example the free base can be dissolved in a mixed aqueous solution of the appropriate acid and the salt recovered by standard techniques, like for example, by evaporation of the solution.

Generally it has been found that the prodrug of this invention is not particularly stable in aqueous solutions. Therefore, effective pharmaceutical compositions include the prodrug in an oil suspension, which may be a mineral oil or an edible vegetable oil. Preferred oil suspensions include the usual triglyceride vegetable oils, preferably the edible oils such as sesame seed oil, cottonseed oil, soybean oil, coconut oil, rapeseed oil, peanut oil, olive oil, palm oil, palm kernel oil, corn oil, castor oil, sunflower seed oil, wallflower oil, and pilchard oil.

The dosage of prodrug in the mydriatic composition of the present invention can comprise from about 0.25% by weight of the composition up to about 10% by weight of the composition which is to be topically applied to the eye. Preferably the composition is from about 0.5% by weight of the prodrug up to about 5% by weight of the prodrug. The balance of the composition is primarily the oil. The preferred oil is sesame seed oil.

The pharmaceutical composition, besides the preferred vegetable oil carrier may contain other non-toxic auxiliary substances such as anti-bacterials, anti-fungals, anti-oxidants, wetting agents, preservatives and the like. Examples include polyethylene glycols 200, 300, 400 and 600, carbowaxes 1,000, 1,500, 4,000 and 10,000; bacterial components such as quaternary ammonium compounds, phenylmercuric salts known to have cold sterilizing properties and which are non-injurious in use, thimerosal, propyl paraben, buffering ingredients such as sodium chloride, sodium borate, sodium acetate, gluconate buffers, and other conventional ingredients such as sorbitan monolaurate, triethanolamine oleate, polyoxyethylene sorbitan monopalmitylate, dioctyl sodium sulfosuccinate, monothioglycerol, thiosorbitol, ethylenediamine tetracetic acid, and the like.

An example of a typical pharmaceutical composition to be used with the compound 2-t-butyl-5-(m-hydroxyphenyl)-1,3-oxazolidine in its base form, includes the following:

| Ingredients | Percent |
| --- | --- |
| Chlorobutanol | 0.25 |
| Methylparaben | 0.05 |
| Propylparaben | 0.01 |
| Wetting Agent, Pluronic P-103 | 0.05 |
| Alpha Topocerol | 0.05 |
| BHT | 0.03 |
| BHA | 0.02 |
| Sesame Seed Oil | Balance |

This composition can also be used with R being $C_2$ to $C_5$ alkyl.

Surprisingly, and it is not known precisely why, the prodrug of the present invention forms a side ring, tying up the amine group of the basic phenylephrine structure, but still upon enzymatic hydrolysis becomes biologically active. Previously it has been believed that if the amine group were sterically interferred with, there would be no mydriatic activity. Moreover, other prodrugs of phenylephrine which have been prepared in the past themselves had undesirable myiocardial side effects. The present ones do not. Moreover, as will be demonstrated in the example, the present compounds are as effective as phenylephrine, at concentrations as low as 10% of that normally used in dosing phenylephrine. It is believed this is so because they are far more effective at absorption through the cornea than phenylephrine itself. Put another way, because they are so quickly absorbed, lower dose levels can be used to produce the same ocular effects. Thus, since the dosage level is lower, the potential risk of side effect is also significantly lower.

The following examples are set forth as illustrative of the present invention but should not be construed as limiting the scope of the invention, since other functionally equivalent means will be readily apparent to those skilled in the art, to use the prodrug invention to achieve similar results.

EXAMPLE 1

Synthesis of Prodrug of Phenylephrine (R)-(-)-phenylephrine base (0.83 g, 5 mmole), pivaldehyde (0.55 ml, 5 mmole) and benzene (100 ml) were refluxed together with stirring for 60 hours under a Dean and Stark trap. The solvent was removed under reduced pressure to yield the oxazolidine prodrug (92% yield). The product was recrystalized from benzene and dried.

Physical Measurements

IR (KBr)–2970, 2870, 1600, 1450, 1400, 1375, 1320, 1265, 1220, 1160, 1120, 1070, 970, 860, 780, 700 $cm^{-1}$.

NMR (CDCl$_3$) $\delta$=7.2–; 6.6 (m, 4H), 5.1–4.8 (m, 1H), (bs, 1,H), 3.5–2.8 (m, 2H), 2.5 (bs, 3H), 1.0 (bs, 9H ppm).

Anal. Calc. for $C_{14}H_{21}NO_2$ : C, 71,46; H, 8.99; N, 5.95. Found: C, 71.71; H, 8.87; N, 5.93.

Dist. Coeff. (DC) log DC = 1.383±0.013.

The reaction as illustrated here is straightforward involving equimolar amounts of reactants phenylephrine and pivaldehyde, refluxed in a suitable solvent. Neither time nor temperature appears critical. In this instance, refluxing and long time were employed to assure complete reaction. Other suitable solvents inert to the reactants could be used.

EXAMPLE 2

Preparation of Phenylephrine Formulations

| Each Contains | Ingredients | Amount Per Batch |
|---|---|---|
| 10.0% | L—Phenylephrine Hydrochloride, U.S.P. | 20.0 gm |
| 0.75% | KH$_2$PO$_4$ anhydrous monopotassium phosphate | 1.50 gm |
| 0.175% | Na$_2$HOP$_4$ anhydrous disodium phosphate | 0.350 gm |
| (+10% excess) | Benzalkonium chloride, N.F. | |
| 0.85% | Methylcellulose U.S.P. 400 cps | 1.70 gm |
| qs 100% | Distilled water | |
| | Fill 55 2 cc ophthalmic containers | qs 200 ml |

Solution Preparation

About 120 ml of water is heated to about 80° C. to which is added the methylcellulose powder. The solution is stirred until all the powder is wetted. The heated solution is then placed in an ice bath and cooled until the methyl-cellulose is fully hydrated or about 45 minutes. To slightly less than 80 ml of water, each ingredient is added until dissolved. Methylcellulose solution is added to the solution containing the other ingredients while stirring. The solution is brought to 200 ml using distilled water.

| Each Contains | Ingredients | Amount Per Batch |
|---|---|---|
| 0.84 or 8.4% | Phenylephrine Oxazolidine* | 1.18 or 16.8 gm |
| 1 or 10% | Phenylephrine HCl* | 2 or 20 gm |
| 0.01% | Pluronic P-103 | 0.02 gm |
| 0.05% | Methylparaben | 0.10 gm |
| 0.01% | Propylparaben | 0.02 gm |
| 0.25% | Chlorabutanol | 0.5 gm |
| Q.S. | Sesame Oil | 200 gm |

*equivalent molar concentrations

Oil Suspension Preparation

Because of the instability of the prodrug aqueous solution, an oil suspension was prepared. The parabens and chlorobutanol are dissolved in about 105 gms of sesame oil. The oil may be heated to about 50° C. to facilitate the dissolution of each ingredient. The pluronic-P103 is incorporated into the drug powder using a motar and pestle. The remaining sesame oil is added to the wetted drug powder and triturated until an acceptable slurry is formed. The sesame oil containing the preservatives is added to the slurry to form the suspension. (Butylated hydroxytolunene (0.03%), butylated hydroxyanisole (0.02%) or alpha tocopherol could be added to stabilize the vegetable oil if long term storage is necessary).

EXAMPLE 3

Mydriatic Experiments

The right eye of a normal adult New Zealand Rabbit (3–4 months) was used to measure mydriasis. A flood of diffuse light was placed at a fixed distance from the rabbit eye so that the initial pupil diameter prior to administering eye drops was about 3 mm. Changes in pupil diameter were measured from photographs taken with a 35 mm single lens reflex camera equipped with a close-up lens. Pupil diameters were measured at time 0 through about 5 hours. A dosing volume of 10 $\mu$l was administered to the right eye of a group of eight rabbits. A period of at least three days was allowed between instillations of each formulation.

FIGS. 1 and 2 give the results. When the 10% oil suspension of phenylephrine HCl was compared to a molar equivalent concentration of phenylephrine oxazolidine (FIG. 1), the oxazolidine prodrug produced a significantly greater mydriasis in the rabbit eye. The results in FIG. 2 indicate to what extent the prodrug is more potent in comparison to a 10% viscous preparation of phenylephrine HCl. Based upon pupillary diameter the prodrug is approximately 10 times more potent than the aqueous solution of phenylephrine HCl.

EXAMPLE 4

A series of experiments were conducted at 35° C. to determine the apparent first order hydrolysis rate constant for phenylephrine oxazolidine at pH's-17.5. The progress of hydrolysis of the prodrug was followed by measuring the production of pivaldehyde subsequently trapped with thiosemicarbazide (pH<4) or semicarbazide (pH 4–7.5). The resulting formation of the carbazone derivative was followed using Uv spectroscopy at 235 and 265 nm (the spectroscopy was a 8450A UV/VIS Hewlett-Packard, Chicago, Ill.). The prodrug was dissolved in either pH 1, 2, 3, 4, 5, 6, 7 or 7.5 buffered aqueous solutions. The buffers used were hydrochloric acid, formate, acetate and phosphate solutions. The carbonyl trapping reagent was included in the buffer solutions at a concentration of $3.1 \times 10(-3)$ M. The initial concentration of oxazolidine prodrug was about $1.8 \times 10(-4)$ M. A volume of 3 ml was used for the reaction which was monitored directly in the absorbance cell. The hydrolysis displayed pseudo-first-order kinetics such that the hydrolysis rate constant could be determined from the slope of a linear ln plot of the amount of carbazone remaining to be formed over time. The concentration of carbazone was calculated by referring to a standard curve.

Results

A half-life of 5–12 minutes was determined for pH's between 1–7.5.

When in the above examples the methyl derivative, i.e. R=C$_1$ is replaced with the C$_2$ to C$_5$ alkyl derivatives substantially similar results are obtained in that a safe and pharmaceutically effective prodrug of phenylephrine is prepared.

It can be seen from the examples presented that the prodrug invention accomplishes all of the enumerated objectives.

What is claimed is:

1. An oxazolidine compound of phenylephrine of the formula:

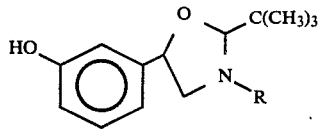

and the non-toxic pharmaceutically acceptable salt forms thereof, wherein R is a $C_1$ to $C_5$ alkyl group.

2. A compound of the formula of claim 1 wherein the compound is 2-t-butyl-3-ethyl-5-(m-hydroxyphenyl)-1,3oxazolidine.

3. A mydriatic composition for topical, ocular application comprising:
a small but mydriatically effective amount of a compound of the formula:

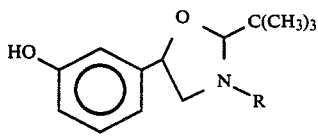

suspended in a non-toxic, non-eye-irritating oil suspension, with R being an alkyl group of $C_1$ to $C_5$.

4. The composition of claim 3 wherein said compound is from about 0.25% by weight to about 10% by weight of the composition.

5. The composition of claim 4 wherein said compound is from about 0.5% by weight to about 5% by weight of said composition.

6. The composition of claim 3 wherein said oil is a mineral oil.

7. The composition of claim 3 wherein said oil is a vegetable oil.

8. The composition of claim 3 wherein said vegetable oil is an edible oil selected from the group consisting of sesame seed oil, cottonseed oil, soybean oil, coconut oil, rapeseed oil, peanut oil, olive oil, palm oil, palm kernel oil, corn oil, sunflower seed oil, castor oil, wallflower oil, and pilchard oil.

9. The composition of claim 8 wherein said oil is sesame seed oil.

10. The composition of claim 3 which includes non-toxic auxiliary substances to enhance the pharmaceutical acceptability of the composition.

11. The composition of claim 1 wherein said non-toxic auxiliary substances include anti-bacterials, anti-fungals, anti-oxidants, wetting agents, preservatives, and the like.

12. A method of topically treating the eye to produce a mydriatic effect comprising:
applying directly to the cornea a small but mydriatically effective amount of a compound of the formula:

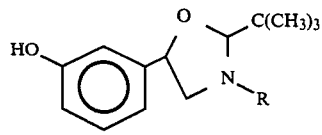

wherein R is an alkyl of from $C_1$ to $C_5$, said compound being suspended in a non-toxic, non-eyeirritating oil suspension.

* * * * *